United States Patent
Ernebrant et al.

(10) Patent No.: US 9,161,980 B2
(45) Date of Patent: Oct. 20, 2015

(54) MEDICAL SOLUTION, A METHOD FOR PRODUCING SAID MEDICAL SOLUTION AND USE THEREOF

(75) Inventors: Malin Ernebrant, Blentarp (SE); Gert-Inge Bertinsson, Lund (SE); Torbjörn Linden, Linderöd (SE); Lars-Fride Olsson, Lund (SE); Theodor Sandström, Lund (SE); Therese Svensson, Genarp (SE); Anders Wieslander, Lund (SE)

(73) Assignee: Gambro Lundia AB, Lund (SE)

( * ) Notice: Subject to any disclaimer, the term of this patent is extended or adjusted under 35 U.S.C. 154(b) by 1669 days.

(21) Appl. No.: 10/591,233

(22) PCT Filed: Feb. 22, 2005

(86) PCT No.: PCT/SE2005/000278
§ 371 (c)(1),
(2), (4) Date: May 7, 2007

(87) PCT Pub. No.: WO2005/082383
PCT Pub. Date: Sep. 9, 2005

(65) Prior Publication Data
US 2007/0298125 A1    Dec. 27, 2007

Related U.S. Application Data

(60) Provisional application No. 60/549,215, filed on Mar. 1, 2004.

(30) Foreign Application Priority Data

Mar. 1, 2004    (SE) ......................... 0400523

(51) Int. Cl.
| | | |
|---|---|---|
| A61K 33/10 | (2006.01) |
| A61K 33/00 | (2006.01) |
| A61K 47/02 | (2006.01) |
| A61K 9/00 | (2006.01) |
| A61K 45/06 | (2006.01) |

(52) U.S. Cl.
CPC ............... *A61K 47/02* (2013.01); *A61K 9/0019* (2013.01); *A61K 33/00* (2013.01); *A61K 33/10* (2013.01); *A61K 45/06* (2013.01)

(58) Field of Classification Search
CPC ... A61K 2300/00; A61K 33/00; A61K 33/10; A61K 45/06; A61K 47/02; A61K 9/0019
See application file for complete search history.

(56) References Cited

U.S. PATENT DOCUMENTS

| | | |
|---|---|---|
| 3,970,750 A | 7/1976 | Brockemeyer et al. |
| 3,993,750 A | 11/1976 | Fox, Jr. |
| 4,548,817 A | 10/1985 | Filley et al. |
| 4,630,727 A | 12/1986 | Feriani et al. |
| 5,211,643 A | 5/1993 | Reinhardt et al. |
| 5,261,872 A | 11/1993 | Goldenberg |
| 5,296,242 A | 3/1994 | Zander |
| 6,017,942 A | 1/2000 | Bergström |
| 6,156,007 A | 12/2000 | Ash |
| 6,277,815 B1 | 8/2001 | Knerr |
| 6,309,673 B1 | 10/2001 | Duponchelle et al. |
| 6,348,162 B1 | 2/2002 | Ash |
| 6,743,191 B1 | 6/2004 | Chang |
| 2008/0085325 A1* | 4/2008 | Carlsson et al. ............... 424/601 |

FOREIGN PATENT DOCUMENTS

| | | |
|---|---|---|
| CN | 1336825 | 2/2002 |
| CN | 1427716 | 7/2003 |
| EP | 0 437 274 | 7/1991 |
| EP | 0 776 649 | 6/1997 |
| EP | 0 643 969 | 12/1998 |
| EP | 0 185 759 | 6/2004 |
| JP | 57091912 | 6/1982 |
| JP | 2000-016484 | 1/2000 |
| WO | WO 83/00293 | 2/1983 |
| WO | WO 86/00227 | 1/1986 |
| WO | WO 91/10457 | 7/1991 |
| WO | WO 98/29434 | 7/1998 |
| WO | WO 01/00204 | 1/2001 |
| WO | WO 0189478 A1 * | 11/2001 |
| WO | WO 03/075982 A1 | 9/2003 |

OTHER PUBLICATIONS

Ing, TS et al. "Increasing plasma phosphorus values by enriching with phosphorus the 'acid concentrate' of a bicarbonate-buffered dialysate delivery system," *The International Journal of Artificial Organs*, 15(12): 701-703 (1992).

International Search Report for PCT/US85/01202, dated Oct. 4, 1985.

Leehey, DJ et al. "Correction of Hypercalcemia and Hypophosphatemia by Hemodialysis Using a Conventional, Calcium-Containing Dialysis Enriched With Phosphorus," *American Journal of Kidney Diseases*, 29(2): 288-290 (1997).

Physicians Desk Reference, 29th Edition, p. 1257 (1974).

Zabaneh, RI et al. "Use of a Phosphorus-Enriched Dialysis Solution to Hemodialyze a Patient with Lithium Intoxication," *Artificial Organs*, 19(1): 94-95 (1995).

* cited by examiner

*Primary Examiner* — Abigail Fisher
(74) *Attorney, Agent, or Firm* — K&L Gates LLP

(57) ABSTRACT

The present invention relates to a medical solution, a method for producing said medical solution, a multi-compartment bag containing the medical solution as well as use of said medical solution. According to the invention the medical solution comprises a first single solution comprising bicarbonate and carbonate in such proportions that the partial pressure of carbon dioxide, $CO_2$, in the first single solution is of the same order of magnitude as the partial pressure of carbon dioxide, $CO_2$, of the atmosphere. The medical solution further comprises a second single solution comprising an acid. Said first and second single solutions are, after terminal sterilization and up on use, to be mixed to form a final solution. Said second single solution has a pH of 1.0-1.5, and said final solution has a pH of 7.0-7.6.

31 Claims, No Drawings

MEDICAL SOLUTION, A METHOD FOR PRODUCING SAID MEDICAL SOLUTION AND USE THEREOF

CROSS REFERENCE TO RELATED APPLICATIONS

This application is a national phase application based on PCT/SE2005/000278, filed Feb. 22, 2005, the content of which is incorporated herein by reference, and claims the priority of Swedish Patent Application No. 0400523-7, filed Mar. 1, 2004, and the benefit of U.S. Provisional Application No. 60/549,215, filed Mar. 1, 2004, the content of both of which is also incorporated herein by reference.

TECHNICAL FIELD OF THE PRESENT INVENTION

The present invention concerns a medical solution, a method for producing said medical solution, a multi-compartment bag containing the medical solution and the use thereof.

BACKGROUND OF THE INVENTION

Medical solutions like dialysis solutions for hemodialysis, hemofiltration, hemodiafiltration, peritoneal dialysis, dialysis within renal intensive care and liquids for substitution or infusion normally contain a buffering substance. Often used buffers are acetate and lactate buffers and these buffers are within the human body metabolized into bicarbonate. Thus, the most physiological buffer in medical solutions would be bicarbonate.

However, the use of bicarbonate as a buffer is more complicated than the use of acetate and lactate for two reasons: First bicarbonate easily precipitates with one of the essential elements in dialysis fluids, viz. calcium, to form calcium carbonate, and second bicarbonate solutions emit carbon dioxide and are thus unstable.

One way to get around the precipitation problem is to separate bicarbonate and calcium in two different containers and then mix them just before use, but the problem with the emitted carbon dioxide still remains.

If carbon dioxide leaves the bicarbonate solution the result is an increase of pH up to 9-10.5 depending on the original bicarbonate concentration. According to prior art, this problem is solved either by use of a gas barrier for carbon dioxide or by allowing the bicarbonate to slowly equilibrate with the atmosphere.

If a gas barrier is used, a complicated and expensive polymer is required as gas barrier otherwise it will result, after mixing with the rest of the content in the container, in an non-definable pH (depending of age of the solution). The polymers used for these types of gas barriers are often very brittle, and care has to be taken when handling and storing the bags with gas barriers not to create cracks that will give rise to leakage.

The idea of letting the bicarbonate slowly equilibrate with the atmosphere is for example disclosed in U.S. Pat. No. 6,309,673. However, this way of solving the problem creates an uncertainty concerning the pH value and the bicarbonate concentration in the final, ready-to-use solution.

In U.S. Pat. No. 5,296,242 a solution is disclosed in which a premix of bicarbonate and carbonate is used in the buffer system. This document discloses a specific mix of bicarbonate and carbonate, which provides for a partial pressure of carbon dioxide that equals the physiological value of the partial pressure within the human body. The buffer solution is further combined with an acid solution, the acid being a metabolizable, organic acid. This reference stresses that an organic acid should be used, this for the therapy of acidosis.

SUMMARY OF THE INVENTION

An object of the invention is to provide a medical solution that, on one hand, ensures good stability, and on the other hand, ensures good biocompatibility.

The present invention provides a medical solution comprising at least two single solutions which, after terminal sterilization and up on use, can be mixed and used as a medical solution. The first single solution comprises bicarbonate and carbonate in such proportions that the partial pressure of carbon dioxide, $CO_2$, in the first single solution is of the same order of magnitude as the partial pressure of carbon dioxide, $CO_2$, of the atmosphere. The second single solution comprises an acid and has a pH of 1.0-1.5. When said first and second single solutions, after terminal sterilization and up on use, are mixed a final solution, ready for use, is formed and it has a pH within the range of 7.0-7.6.

By ensuring that the partial pressure of carbon dioxide, $CO_2$, in the first single solution is of the same order of magnitude as the partial pressure of carbon dioxide, $CO_2$, of the atmosphere, there is no driving force which urges carbon dioxide out from the container in which the solutions are contained. Accordingly, the carbonate and bicarbonate concentrations will be stable and the problem with the solutions of prior art is overcome.

In a preferred embodiment of the present invention said first single solution has a pH of 10.1-10.5, preferably 10.3.

Said second single solution preferably has a pH of 1.3. Preferably, said second single solution is acidified by hydrochloric acid, HCl.

According to another preferred embodiment of the present invention the medical solution further comprises one or more osmotic agents. Preferred said one or more osmotic agents are chosen among glucose, glucose polymers, glycerol, xylitol, fructose, amino acids, peptides, proteins, amino sugars, N-acetyl glucose amine (NAG), or combinations thereof.

In one preferred embodiment of the present invention said one or more osmotic agents are, before being mixed into the final solution, arranged in said second single solution. In another preferred embodiment, said one or more osmotic agents are arranged in a third single solution before being mixed into the final solution. In even another preferred embodiment, said one or more osmotic agents are also arranged in a fourth single solution before being mixed into the final solution.

In a preferred embodiment, said one or more osmotic agents in said third and fourth single solutions is glucose and/or glucose polymers, which could give rise to glucose degradation products (GDPs) during terminal sterilization and/or storage. If this is the case, said third and fourth single solutions comprise an acid and have a pH of at least 1.8, preferably at least 2.0, and a pH of at most 2.6, preferably at most 2.5, and most preferably at most 2.3.

According to another preferred embodiment of the present invention the final solution further comprises one or more electrolytes. The one or more electrolytes comprise according to one preferred embodiment of the invention one or more of the ions of sodium, calcium, potassium, magnesium and/or chloride. These one or more electrolytes could, according to different preferred embodiments of the present invention, before being mixed into the final solution, be included in said first single solution, in said second single solution, and/or in said optional third and/or fourth single solution. However, magnesium and/or calcium should not be included in said first single solution, as magnesium and calcium will precipitate as magnesium carbonate and calcium carbonate, respectively, when included in the first single solution together with carbonate and bicarbonate.

In another preferred embodiment of the invention, the different single solutions are provided in different compartments in a multi-compartment bag before being mixed to the final solution.

The present invention further provides for a method for producing said medical solution. According to the invention the method comprises providing said single solutions in separate compartments, and thereafter terminally sterilizing said single solutions.

According to a preferred embodiment of the method according to the present invention said terminal sterilization is heat sterilization and/or radiation sterilization. In an even more preferred embodiment of the method according to the present invention, said terminal sterilization is heat sterilization at a temperature of at least 100° C., preferably at least 121° C.

In a preferred embodiment of the invention said first and second single solutions, after sterilization and up on use, are mixed to form a final solution. In another preferred embodiment said first, second and third single solutions, after sterilization and up on use, are mixed to form a final solution. In another preferred embodiment of the invention, said first, second and fourth single solutions, after sterilization and up on use, are mixed to form a final solution, and in even another preferred embodiment of the invention, said first, second, third and fourth single solutions, after sterilization and up on use, are mixed to form a final solution.

The present invention further provides a multi-compartment bag comprising the medical solution according to above and the use of the medical solution according to above.

Additional objects, features, advantages and preferred embodiments of the present invention will become apparent from the following detailed description when taken in conjunction with the enclosed patent claims.

DEFINITIONS

The term "medical solution" is intended to mean dialysis solutions for hemodialysis, hemodiafiltration, hemofiltration, and peritoneal dialysis, solutions for dialysis within renal intensive care, solutions for substitution or infusion normally containing buffering substances, and solutions for nutrition purposes.

The term "single solution" is intended to mean one solution kept isolated from other solutions up until use.

The term "bicarbonate and carbonate" is intended to mean alkali bicarbonate and alkali carbonate, especially sodium bicarbonate and sodium carbonate.

The term "a final solution" is intended to mean the solution which includes the required different single solutions and which is ready for use.

The term "multi-compartment bag" is intended to mean bag divided into more than one compartment and that the content in the different compartments could be brought together and mixed before use.

The term "terminal sterilization" is intended to mean that the product is sterilized in its final package. The terminal sterilization may include heat sterilization and/or radiation sterilization, but is preferably heat sterilization effected in an autoclave at a temperature of at least 100° C., preferably at least 121° C.

The term "up on use" is intended to mean as close as possible before the medical solution is used for its specific purpose.

DETAILED DESCRIPTION OF THE INVENTION

The medical solution according to the invention comprises a first single solution and a second single solution, wherein said first and second single solutions, after terminal sterilization and up on use, are to be mixed to form a final solution.

Said first single solution comprises bicarbonate and carbonate in such proportions that the partial pressure of carbon dioxide, $CO_2$, in the first single solution is of the same order of magnitude as the partial pressure of carbon dioxide, $CO_2$, of the atmosphere. Preferably, bicarbonate and carbonate are mixed as sodium bicarbonate and sodium carbonate. Preferably, said first single solution has a pH within the range of 10.1-10.5, most preferably said first single solution has a pH of 10.3.

After having mixed at least said first and second single solutions into a final solution, said final solution has a pH within the range of 7.0-7.6. Further, said final solution preferably has a bicarbonate concentration of at least 25 mM, preferably at least 30 mM, and at most 45 mM, preferably at most 40 mM.

Said second single solution has preferably a pH within the range of 1.0-1.5, most preferably a pH of 1.3. In a preferred embodiment of the invention said second single solution comprises HCl.

The medical solution according to the invention preferably comprises one or more osmotic agents that are preferably chosen among glucose, glucose polymers, glycerol, xylitol, fructose, amino acids, peptides, proteins, amino sugars, N-acetyl glucose amine (NAG), or combinations thereof. The one or more osmotic agents are in one preferred embodiment, before being mixed into the final solution, arranged in said second single solution. However, in another preferred embodiment the one or more osmotic agents are arranged in a third single solution. In even another preferred embodiment of the invention, said one or more osmotic agents are, before being mixed into said final solution besides being arranged in a third single solution, also arranged in a fourth single solution.

In case of using one or more osmotic agents, which could give rise to glucose degradation products, said third and fourth single solutions further comprise an acid and preferably have a pH of at least 1.8, preferably at least 2.0, and a pH of at most 2.6, preferably at most 2.5 and most preferably at most 2.3. Within these pH ranges the amount of the glucose degradation products (GDPs) being most toxic is as low as possible, and especially 3,4-dideoxyglucosone-3-ene (3,4-DGE), which is the most toxic one of all the GDPs. GDPs are known to give rise to several problems during for example peritoneal dialysis and of course it is always an aim to reduce the amount of toxic substances. However, besides optimizing the pH of said third and forth single solutions, it is also important to keep the concentration of one or more osmotic agents, which could give rise to GDPs, of at least 10% by weight, preferably at least 20% by weight and most preferably at least 40% by weight, based on the total weight of said third and fourth single solutions, respectively.

In a preferred embodiment of the invention said third and fourth single solutions could comprise different total amounts of one or more osmotic agents. The different total amounts could be achieved by providing the same concentrations within said third and fourth single solutions, but providing different volumes thereof. The different total amounts could also be achieved by providing the same volume of said third and fourth single solutions, but providing different concentrations in said third single solution in comparison with said fourth single solution. By having such a preferred medical solution comprising said first, second, third and fourth single solutions, the user thereof could choose what concentration of osmotic agent the user would like to have for a specific treatment. By combining said first, second and third single solutions to a final solution, the user gets a first specific concentration of osmotic agent, by combining said first, second and fourth single solutions to a final solution, the user gets a second specific concentration of osmotic agent, and by combining said first, second, third and fourth single solutions to a final solution, the user gets a third specific concentration of osmotic agent. Accordingly, said third and fourth single solutions could, up on use, be mixed individually, with said first and second solutions, i.e. either first, second and third, or first, second and fourth, or jointly, i.e. mixing first, second, third and fourth single solutions together. Note that said final solution always have a pH within the range of 7.0-7.6, no matter which of the above combinations of single solutions is used. The buffer solution in said first single solution have the capability to buffer said third and/or fourth single solution(s) in combination with said second single solution to a final solution with a pH of 7.0-7.6.

In a preferred embodiment of the invention the medical solution further contains one or more electrolytes. Preferably, the electrolytes is one or more of the ions of sodium, calcium, potassium, magnesium and chloride.

The arrangement of electrolytes in the different compartments is dependent on the different electrolytes co-behavior with the other substances present in the single solutions, i.e. whether some sort of reaction could occur between one or more of the electrolyte(s) and the other substances present in a specific single solution. Usually, the electrolytes are contained in said second single solution. For example, calcium and magnesium ions are preferably provided in any of the other single solutions, but said first single solution. The reason for this is that calcium and magnesium together with bicarbonate and/or carbonate could cause precipitation of calcium carbonate and magnesium carbonate, respectively. However, calcium ions could be kept with bicarbonate under certain circumstances, such as specific pH ranges and so on, this is for example disclosed in EP 0 437 274, which hereby is enclosed by reference.

In the method for producing a medical solution according to above, said single solutions are provided in separate compartments. Thereafter said single solutions are terminally sterilized. Preferably, the terminal sterilization is heat sterilization and/or radiation sterilization, (see also European Pharmacopoeia 1977 for a review of different sterilization techniques). In a preferred embodiment of the method according to the invention, the terminal sterilization is heat sterilization at a temperature of at least 100° C., preferably at least 121° C.

The sterilization time may vary depending on the sterilization temperature, the type of container and the contents therein to be sterilized.

The radiation sterilization may be either ionising or non-ionising sterilization. Examples of ionising sterilization are gamma and beta radiation. Examples of non-ionising radiation sterilization is UV radiation.

The medical solution according to the present invention has the advantage of ensuring good stability and good biocompatibility.

Said single solutions could be provided in different compartments in a multi-compartment bag, and the mixing could be provided by having the different compartments sealingly coupled by frangible pins, which different pins could be broken in order to mix the content in optional compartments within the multicompartment bag. The mixing could further be provided by having a peal seal in-between the different compartments, which peal seals could be pealed in order to mix the content in the different compartments.

Below you will find different examples of solutions according to the present invention.

EXAMPLES

By way of example, and not limitation, the following examples identify a variety of solutions made pursuant to an embodiment of the present invention.

Example 1-4

Two Compartment Bags

| Compartment 1: | | | | |
|---|---|---|---|---|
| | Example 1 | Example 2 | Example 3 | Example 4 |
| $NaHCO_3$ | 95.5 mM | 95.5 mM | 112 mM | 112 mM |
| $Na_2CO_3$ | 304.5 mM | 304.5 mM | 258 mM | 258 mM |
| pH | 10.3 | 10.3 | 10.3 | 10.3 |
| Volume | 0.5 l | 0.5 l | 0.5 l | 0.5 l |

| Compartment 2: | | | | |
|---|---|---|---|---|
| | Example 1 | Example 2 | Example 3 | Example 4 |
| HCl | 38 mM | 38 mM | 38 mM | 38 mM |
| NaCl | 77.3 mM | 77.3 mM | 77.3 mM | 77.3 mM |
| $CaCl_2 \cdot 2H_2O$ | 1.95 mM | 1.95 mM | 1.95 mM | 1.95 mM |
| $MgCl_2 \cdot 6H_2O$ | 0.56 mM | 0.56 mM | 0.56 mM | 0.56 mM |
| Glucose | — | 1.22 g/l | — | 1.22 g/l |
| Lactate | — | — | 3.30 mM | 3.30 mM |
| pH | 1.3 | 1.3 | 1.3 | 1.3 |
| Volume | 4.5 l | 4.5 l | 4.5 l | 4.5 l |

| Solution, mixed and ready for use: | | | | |
|---|---|---|---|---|
| | Example 1 | Example 2 | Example 3 | Example 4 |
| Volume | 5 l | 5 l | 5 l | 5 l |
| pH | 7.25 | 7.25 | 7.25 | 7.25 |
| $Cl^-$ | 108.3 mM | 108.3 mM | 108.3 mM | 108.3 mM |
| $Na^+$ | 140.02 mM | 140.02 mM | 135.37 mM | 135.37 mM |
| $Ca^+$ | 1.76 mM | 1.76 mM | 1.76 mM | 1.76 mM |
| $Mg^+$ | 0.5 mM | 0.5 mM | 0.5 mM | 0.5 mM |
| $HCO3^-$ | 40 mM | 40 mM | 37 mM | 37 mM |
| Glucose | — | 1.1 g/l | — | 1.1 g/l |
| Lactate | — | — | 3 mM | 3 mM |

Example 5-8

Two Compartment Bags

Compartment 1:

|  | Example 5 | Example 6 | Example 7 | Example 8 |
|---|---|---|---|---|
| NaHCO$_3$ | 139 mM | 139 mM | 133 mM | 133 mM |
| Na$_2$CO$_3$ | 661 mM | 661 mM | 607 mM | 607 mM |
| pH | 10.3 | 10.3 | 10.3 | 10.3 |
| Volume | 0.25 l | 0.25 l | 0.25 l | 0.25 l |

Compartment 2:

|  | Example 5 | Example 6 | Example 7 | Example 8 |
|---|---|---|---|---|
| HCl | 38.4 mM | 38.4 mM | 38.4 mM | 38.4 mM |
| NaCl | 70.5 mM | 70.5 mM | 70.5 mM | 70.5 mM |
| CaCl$_2$*2H$_2$O | 1.84 mM | 1.84 mM | 1.84 mM | 1.84 mM |
| MgCl$_2$*6H$_2$O | 0.53 mM | 0.53 mM | 0.53 mM | 0.53 mM |
| Glucose | — | 1.16 g/l | — | 1.16 g/l |
| Lactate | — | — | 3.16 mM | 3.16 mM |
| pH | 1.3 | 1.3 | 1.3 | 1.3 |
| Volume | 4.75 l | 4.75 l | 4.75 l | 4.75 l |

Solution, mixed and ready for use:

|  | Example 5 | Example 6 | Example 7 | Example 8 |
|---|---|---|---|---|
| Volume | 5 l | 5 l | 5 l | 5 l |
| pH | 7.25 | 7.25 | 7.25 | 7.25 |
| Cl$^-$ | 107.6 mM | 107.6 mM | 107.6 mM | 107.6 mM |
| Na$^+$ | 140.03 mM | 140.03 mM | 137.18 mM | 137.18 mM |
| Ca$^+$ | 1.75 mM | 1.75 mM | 1.75 mM | 1.75 mM |
| Mg$^+$ | 0.5 mM | 0.5 mM | 0.5 mM | 0.5 mM |
| HCO3$^-$ | 40 mM | 40 mM | 37 mM | 37 mM |
| Glucose | — | 1.1 g/l | — | 1.1 g/l |
| Lactate | — | — | 3 mM | 3 mM |

Examples 9-12

Three Compartment Bags

Compartment 1:

|  | Example 9 | Example 10 | Example 11 | Example 12 |
|---|---|---|---|---|
| NaHCO$_3$ | 95.5 mM | 112 mM | 139 mM | 133 mM |
| Na$_2$CO$_3$ | 304.5 mM | 258 mM | 661 mM | 607 mM |
| pH | 10.3 | 10.3 | 10.3 | 10.3 |
| Volume | 0.2 l | 0.2 l | 0.1 l | 0.1 l |

Compartment 2:

|  | Example 9 | Example 10 | Example 11 | Example 12 |
|---|---|---|---|---|
| HCl | 41.02 mM | 41.02 mM | 39.23 mM | 39.23 mM |
| NaCl | 83.45 mM | 83.45 mM | 72.02 mM | 72.02 mM |
| CaCl$_2$*2H$_2$O | 2.11 mM | 2.11 mM | 1.88 mM | 1.88 mM |
| MgCl$_2$*6H$_2$O | 0.60 mM | 0.60 mM | 0.54 mM | 0.54 mM |
| Glucose | 17.05 | 17.05 g/l | 16.13 g/l | 16.13 g/l |
| Lactate | — | 3.41 mM | — | 3.23 mM |
| pH | 1.3 | 1.3 | 1.3 | 1.3 |
| Volume | 1.76 l | 1.76 l | 1.86 l | 1.86 l |

Third compartment:

|  | Example 9 | Example 10 | Example 11 | Example 12 |
|---|---|---|---|---|
| Glucose | 500 g/l | 500 g/l mM | 500 g/lmM | 500 g/l |
| pH | 2-2.5 | 2-2.5 | 2-2.5 | 2-2.5 |
| Volume | 0.04 l | 0.04 l | 0.04 l | 0.04 l |

Solution, mixed and ready for use:

|  | Example 9 | Example 10 | Example 11 | Example 12 |
|---|---|---|---|---|
| Volume | 2 l | 2 l | 2 l | 2 l |
| pH | 7.25 | 7.25 | 7.25 | 7.25 |
| Cl$^-$ | 108.3 mM | 108.3 mM | 107.96 mM | 107.96 mM |
| Na$^+$ | 140.02 mM | 135.37 mM | 140.03 mM | 140.03 mM |
| Ca$^+$ | 1.76 mM | 1.76 mM | 1.75 mM | 1.75 mM |
| Mg$^+$ | 0.5 mM | 0.5 mM | 0.5 mM | 0.5 mM |
| HCO3$^-$ | 40 mM | 37 mM | 40 mM | 40 mM |
| Glucose | 15/25 g/l* | 15/25 g/l* | 15/25 g/l* | 15/25 g/l* |
| Lactate | — | 3 mM | — | 3 mM |

*15 g/l is compartment 1 and 2 are mixed and 25 g/l if all three compartments are mixed.

Examples 13-16

Four-Compartment Bags

Compartment 1:

|  | Example 13 | Example 14 | Example 15 | Example 16 |
|---|---|---|---|---|
| NaHCO$_3$ | 95.5 mM | 112 mM | 139 mM | 133 mM |
| Na$_2$CO$_3$ | 304.5 mM | 258 mM | 661 mM | 607 mM |
| pH | 10.3 | 10.3 | 10.3 | 10.3 |
| Volume | 0.196 l | 0.196 l | 0.098 l | 0.098 l |

Compartment 2:

|  | Example 13 | Example 14 | Example 15 | Example 16 |
|---|---|---|---|---|
| HCl | 38.78 mM | 38.78 mM | 39.18 mM | 39.18 mM |
| NaCl | 78.88 mM | 78.88 mM | 71.94 mM | 71.94 mM |
| CaCl$_2$*2H$_2$O | 1.99 mM | 1.99 mM | 1.88 mM | 1.88 mM |
| MgCl$_2$*6H$_2$O | 0.57 mM | 0.57 mM | 0.54 mM | 0.54 mM |
| Lactate | — | 3.41 mM | — | 3.22 mM |
| pH | 1.3 | 1.3 | 1.3 | 1.3 |
| Volume | 1.764 l | 1.764 l | 1.862 l | 1.862 l |

Third compartment:

|  | Example 13 | Example 14 | Example 15 | Example 16 |
|---|---|---|---|---|
| Glucose | 500 g/l | 500 g/l | 500 g/l | 500 g/l |
| pH | 2-2.5 | 2-2.5 | 2-2.5 | 2-2.5 |
| Volume | 0.062 l | 0.062 l | 0.062 l | 0.062 l |

Fourth compartment:

|  | Example 13 | Example 14 | Example 15 | Example 16 |
|---|---|---|---|---|
| Glucose | 500 g/l | 500 g/l | 500 g/l | 500 g/l |
| pH | 2-2.5 | 2-2.5 | 2-2.5 | 2-2.5 |
| Volume | 0.103 l | 0.103 l | 0.103 l | 0.103 l |

Solution, mixed and ready for use:

|  | Compartment 1 + 2 + 3 | Compartment 1 + 2 + 4 | Compartment 1 + 2 + 3 + 4 |
|---|---|---|---|
| Example 13 | | | |
| Volume | 2.022 l | 2.063 l | 2.125 l |
| pH | 7.25 | 7.25 | 7.25 |
| $Cl^-$ | 107.1 mM | 105.0 mM | 101.9 mM |
| $Na^+$ | 137.1 mN | 134.4 mM | 130.5 mM |
| $Ca^+$ | 1.74 mM | 1.70 mM | 1.65 mM |
| $Mg^+$ | 0.50 mM | 0.49 mM | 0.47 mM |
| $HCO_3^-$ | 38.8 mM | 38.0 mM | 36.9 mM |
| Glucose | 15.3 g/l | 25.0 g/l | 38.8 g/l |
| Example 14 | | | |
| Volume | 2.022 l | 2.063 l | 2.125 l |
| pH | 7.25 | 7.25 | 7.25 |
| $Cl^-$ | 107.1 mM | 105.0 mM | 101.9 mM |
| $Na^+$ | 135.6 mM | 132.9 mM | 129.1 mM |
| $Ca^+$ | 1.74 mM | 1.70 mM | 1.65 mM |
| $Mg^+$ | 0.50 mM | 0.49 mM | 0.47 mM |
| $HCO_3^-$ | 35.9 mM | 35.2 mM | 34.1 mM |
| Glucose | 15.3 g/l | 25.0 g/l | 38.8 g/l |
| Lactate | 2.98 mM | 2.92 mM | 2.83 mM |
| Example 15 | | | |
| Volume | 2.022 l | 2.063 l | 2.125 l |
| pH | 7.25 | 7.25 | 7.25 |
| $Cl^-$ | 106.8 mM | 104.7 mM | 101.6 mM |
| $Na^+$ | 137.1 mM | 134.3 mM | 130.5 mM |
| $Ca^+$ | 1.73 mM | 1.70 mM | 1.65 mM |
| $Mg^+$ | 0.50 mM | 0.49 mM | 0.47 mM |
| $HCO_3^-$ | 38.8 mM | 38.0 mM | 36.9 mM |
| Glucose | 15.3 g/l | 25.0 g/l | 38.8 g/l |
| Example 16 | | | |
| Volume | 2.022 l | 2.063 l | 2.125 l |
| pH | 7.25 | 7.25 | 7.25 |
| $Cl^-$ | 106.8 mM | 104.7 mM | 101.6 mM |
| $Na^+$ | 137.5 mM | 134.7 mM | 130.8 mM |
| $Ca^+$ | 1.73 mM | 1.70 mM | 1.65 mM |
| $Mg^+$ | 0.5 mM | 0.49 mM | 0.47 mM |
| $HCO_3^-$ | 38.8 mM | 38.0 mM | 36.9 mM |
| Glucose | 15.3 g/l | 25.0 g/l | 38.8 g/l |
| Lactate | 2.97 mM | 2.91 mM | 2.82 mM |

Example 17-20

Two Compartment Bags

Compartment 1:

|  | Example 17 | Example 18 | Example 19 | Example 20 |
|---|---|---|---|---|
| $NaHCO_3$ | 95.5 mM | 95.5 mM | 112 mM | 112 mM |
| $Na_2CO_3$ | 304.5 mM | 304.5 mM | 258 mM | 258 mM |
| pH | 10.3 | 10.3 | 10.3 | 10.3 |
| Volume | 0.5 l | 0.5 l | 0.5 l | 0.5 l |

Compartment 2:

|  | Example 17 | Example 18 | Example 19 | Example 20 |
|---|---|---|---|---|
| HCl | 35.5 mM | 35.5 mM | 35.5 mM | 35.5 mM |
| NaCl | 77.3 mM | 77.3 mM | 77.3 mM | 77.3 mM |
| $CaCl_2*2H_2O$ | 1.95 mM | 1.95 mM | 1.95 mM | 1.95 mM |
| $MgCl_2*6H_2O$ | 0.56 mM | 0.56 mM | 0.56 mM | 0.56 mM |
| Glucose | — | 1.22 g/l | — | 1.22 g/l |
| Lactate | — | — | 3.30 mM | 3.30 mM |
| pH | 1.3 | 1.3 | 1.3 | 1.3 |
| Volume | 4.5 l | 4.5 l | 4.5 l | 4.5 l |

Solution, mixed and ready for use:

|  | Example 17 | Example 18 | Example 19 | Example 20 |
|---|---|---|---|---|
| Volume | 5 l | 5 l | 5 l | 5 l |
| pH | 7.5 | 7.5 | 7.5 | 7.5 |
| $Cl^-$ | 106.03 mM | 106.03 mM | 106.03 mM | 106.03 mM |
| $Na^+$ | 140.02 mM | 140.02 mM | 135.37 mM | 135.37 mM |
| $Ca^+$ | 1.76 mM | 1.76 mM | 1.76 mM | 1.76 mM |
| $Mg^+$ | 0.5 mM | 0.5 mM | 0.5 mM | 0.5 mM |
| HCO3− | 40 mM | 40 mM | 37 mM | 37 mM |
| Glucose | — | 1.1 g/l | — | 1.1 g/l |
| Lactate | — | — | 3 mM | 3 mM |

Example 21-24

Two Compartment Bags

Compartment 1:

|  | Example 21 | Example 22 | Example 23 | Example 24 |
|---|---|---|---|---|
| $NaHCO_3$ | 139 mM | 139 mM | 133 mM | 133 mM |
| $Na_2CO_3$ | 661 mM | 661 mM | 607 mM | 607 mM |
| pH | 10.3 | 10.3 | 10.3 | 10.3 |
| Volume | 0.25 l | 0.25 l | 0.25 l | 0.25 l |

Compartment 2:

|  | Example 21 | Example 22 | Example 23 | Example 24 |
|---|---|---|---|---|
| HCl | 36.11 mM | 36.11 mM | 36.11 mM | 36.11 mM |
| NaCl | 70.5 mM | 70.5 mM | 70.5 mM | 70.5 mM |
| $CaCl_2*2H_2O$ | 1.84 mM | 1.84 mM | 1.84 mM | 1.84 mM |
| $MgCl_2*6H_2O$ | 0.53 mM | 0.53 mM | 0.53 mM | 0.53 mM |

-continued

| Compartment 2: | | | | |
|---|---|---|---|---|
| | Example 21 | Example 22 | Example 23 | Example 24 |
| Glucose | — | 1.16 g/l | — | 1.16 g/l |
| Lactate | — | — | 3.16 mM | 3.16 mM |
| pH | 1.3 | 1.3 | 1.3 | 1.3 |
| Volume | 4.75 l | 4.75 l | 4.75 l | 4.75 l |

| Solution, mixed and ready for use: | | | | |
|---|---|---|---|---|
| | Example 21 | Example 22 | Example 23 | Example 24 |
| Volume | 5 l | 5 l | 5 l | 5 l |
| pH | 7.5 | 7.5 | 7.5 | 7.5 |
| Cl$^-$ | 105.78 mM | 105.78 mM | 105.78 mM | 105.78 mM |
| Na$^+$ | 140.03 mM | 140.03 mM | 137.18 mM | 137.18 mM |
| Ca$^+$ | 1.75 mM | 1.75 mM | 1.75 mM | 1.75 mM |
| Mg$^+$ | 0.5 mM | 0.5 mM | 0.5 mM | 0.5 mM |
| HCO3$^-$ | 40 mM | 40 mM | 37 mM | 37 mM |
| Glucose | — | 1.1 g/l | — | 1.1 g/l |
| Lactate | — | — | 3 mM | 3 mM |

Example 25-28

Two Compartment Bags

| Compartment 1: | | | | |
|---|---|---|---|---|
| | Example 25 | Example 26 | Example 27 | Example 28 |
| NaHCO$_3$ | 95.5 mM | 95.5 mM | 112 mM | 112 mM |
| Na$_2$CO$_3$ | 304.5 mM | 304.5 mM | 258 mM | 258 mM |
| pH | 10.3 | 10.3 | 10.3 | 10.3 |
| Volume | 0.5 l | 0.5 l | 0.5 l | 0.5 l |

| Compartment 2: | | | | |
|---|---|---|---|---|
| | Example 25 | Example 26 | Example 27 | Example 28 |
| HCl | 38.74 mM | 38.74 mM | 38.74 mM | 38.74 mM |
| NaCl | 77.3 mM | 77.3 mM | 77.3 mM | 77.3 mM |
| CaCl$_2$*2H$_2$O | 1.95 mM | 1.95 mM | 1.95 mM | 1.95 mM |
| MgCl$_2$*6H$_2$O | 0.56 mM | 0.56 mM | 0.56 mM | 0.56 mM |
| Glucose | — | 1.22 g/l | — | 1.22 g/l |
| Lactate | — | — | 3.30 mM | 3.30 mM |
| pH | 1.3 | 1.3 | 1.3 | 1.3 |
| Volume | 4.5 l | 4.5 l | 4.5 l | 4.5 l |

| Solution, mixed and ready for use: | | | | |
|---|---|---|---|---|
| | Example 25 | Example 26 | Example 27 | Example 28 |
| Volume | 5 l | 5 l | 5 l | 5 l |
| pH | 7.0 | 7.0 | 7.0 | 7.0 |
| Cl$^-$ | 108.95 mM | 108.95 mM | 108.95 mM | 108.95 mM |
| Na$^+$ | 140.02 mM | 140.02 mM | 135.37 mM | 135.37 mM |
| Ca$^+$ | 1.76 mM | 1.76 mM | 1.76 mM | 1.76 mM |
| Mg$^+$ | 0.5 mM | 0.5 mM | 0.5 mM | 0.5 mM |
| HCO3$^-$ | 40 mM | 40 mM | 37 mM | 37 mM |
| Glucose | — | 1.1 g/l | — | 1.1 g/l |
| Lactate | — | — | 3 mM | 3 mM |

Example 29-32

Two Compartment Bags

| Compartment 1: | | | | |
|---|---|---|---|---|
| | Example 29 | Example 30 | Example 31 | Example 32 |
| NaHCO$_3$ | 139 mM | 139 mM | 133 mM | 133 mM |
| Na$_2$CO$_3$ | 661 mM | 661 mM | 607 mM | 607 mM |
| pH | 10.3 | 10.3 | 10.3 | 10.3 |
| Volume | 0.25 l | 0.25 l | 0.25 l | 0.25 l |

| Compartment 2: | | | | |
|---|---|---|---|---|
| | Example 29 | Example 30 | Example 31 | Example 32 |
| HCl | 39.19 mM | 39.19 mM | 39.19 mM | 39.19 mM |
| NaCl | 70.5 mM | 70.5 mM | 70.5 mM | 70.5 mM |
| CaCl$_2$*2H$_2$O | 1.84 mM | 1.84 mM | 1.84 mM | 1.84 mM |
| MgCl$_2$*6H$_2$O | 0.53 mM | 0.53 mM | 0.53 mM | 0.53 mM |
| Glucose | — | 1.16 g/l | — | 1.16 g/l |
| Lactate | — | — | 3.16 mM | 3.16 mM |
| pH | 1.3 | 1.3 | 1.3 | 1.3 |
| Volume | 4.75 l | 4.75 l | 4.75 l | 4.75 l |

| Solution, mixed and ready for use: | | | | |
|---|---|---|---|---|
| | Example 29 | Example 30 | Example 31 | Example 32 |
| Volume | 5 l | 5 l | 5 l | 5 l |
| pH | 7.0 | 7.0 | 7.0 | 7.0 |
| Cl$^-$ | 108.71 mM | 108.71 mM | 108.71 mM | 108.71 mM |
| Na$^+$ | 140.03 mM | 140.03 mM | 137.18 mM | 137.18 mM |
| Ca$^+$ | 1.75 mM | 1.75 mM | 1.75 mM | 1.75 mM |
| Mg$^+$ | 0.5 mM | 0.5 mM | 0.5 mM | 0.5 mM |
| HCO3$^-$ | 40 mM | 40 mM | 37 mM | 37 mM |
| Glucose | — | 1.1 g/l | — | 1.1 g/l |
| Lactate | — | — | 3 mM | 3 mM |

Examples 33-36

Four-Compartment Bags

| Compartment 1: | | | | |
|---|---|---|---|---|
| | Example 33 | Example 34 | Example 35 | Example 36 |
| NaHCO$_3$ | 95.5 mM | 112 mM | 139 mM | 133 mM |
| Na$_2$CO$_3$ | 304.5 mM | 258 mM | 661 mM | 607 mM |
| pH | 10.3 | 10.3 | 10.3 | 10.3 |
| Volume | 0.196 l | 0.196 l | 0.098 l | 0.098 l |

Compartment 2:

| | Example 33 | Example 34 | Example 35 | Example 36 |
|---|---|---|---|---|
| HCl | 38.74 mM | 38.74 mM | 39.19 mM | 39.19 mM |
| NaCl | 78.88 mM | 78.88 mM | 71.94 mM | 71.94 mM |
| $CaCl_2 \cdot 2H_2O$ | 1.99 mM | 1.99 mM | 1.88 mM | 1.88 mM |
| $MgCl_2 \cdot 6H_2O$ | 0.57 mM | 0.57 mM | 0.54 mM | 0.54 mM |
| Lactate | — | 3.41 mM | — | 3.22 mM |
| pH | 1.3 | 1.3 | 1.3 | 1.3 |
| Volume | 1.764 l | 1.764 l | 1.862 l | 1.862 l |

Third compartment:

| | Example 33 | Example 34 | Example 35 | Example 36 |
|---|---|---|---|---|
| Glucose | 500 g/l | 500 g/l | 500 g/l | 500 g/l |
| pH | 2-2.5 | 2-2.5 | 2-2.5 | 2-2.5 |
| Volume | 0.062 l | 0.062 l | 0.062 l | 0.062 l |

Fourth compartment:

| | Example 33 | Example 34 | Example 35 | Example 36 |
|---|---|---|---|---|
| Glucose | 500 g/l | 500 g/l | 500 g/l | 500 g/l |
| pH | 2-2.5 | 2-2.5 | 2-2.5 | 2-2.5 |
| Volume | 0.103 l | 0.103 l | 0.103 l | 0.103 l |

Solution, mixed and ready for use:

| | Compartment 1 + 2 + 3 | Compartment 1 + 2 + 4 | Compartment 1 + 2 + 3 + 4 |
|---|---|---|---|
| Example 33 | | | |
| Volume | 2.022 l | 2.063 l | 2.125 l |
| pH | 7.0 | 7.0 | 7.0 |
| $Cl^-$ | 107.8 mM | 105.6 mM | 102.5 mM |
| $Na^+$ | 137.1 mM | 134.4 mM | 130.5 mM |
| $Ca^+$ | 1.74 mM | 1.70 mM | 1.65 mM |
| $Mg^+$ | 0.50 mM | 0.49 mM | 0.47 mM |
| $HCO_3^-$ | 38.8 mM | 38.0 mM | 36.9 mM |
| Glucose | 15.3 g/l | 25.0 g/l | 38.8 g/l |
| Example 34 | | | |
| Volume | 2.022 l | 2.063 l | 2.125 l |
| pH | 7.0 | 7.0 | 7.0 |
| $Cl^-$ | 107.8 mM | 105.6 mM | 102.5 mM |
| $Na^+$ | 135.6 mM | 132.9 mM | 129.1 mM |
| $Ca^+$ | 1.74 mM | 1.70 mM | 1.65 mM |
| $Mg^+$ | 0.50 mM | 0.49 mM | 0.47 mM |
| $HCO_3^-$ | 35.9 mM | 35.2 mM | 34.1 mM |
| Glucose | 15.3 g/l | 25.0 g/l | 38.8 g/l |
| Lactate | 2.98 mM | 2.92 mM | 2.83 mM |
| Example 35 | | | |
| Volume | 2.022 l | 2.063 l | 2.125 l |
| pH | 7.0 | 7.0 | 7.0 |
| $Cl^-$ | 113.2 mM | 110.9 mM | 107.7 mM |
| $Na^+$ | 137.1 mM | 134.3 mM | 130.5 mM |
| $Ca^+$ | 1.73 mM | 1.70 mM | 1.65 mM |
| $Mg^+$ | 0.50 mM | 0.49 mM | 0.47 mM |
| $HCO_3^-$ | 38.8 mM | 38.0 mM | 36.9 mM |
| Glucose | 15.3 g/l | 25.0 g/l | 38.8 g/l |
| Example 36 | | | |
| Volume | 2.022 l | 2.063 l | 2.125 l |
| pH | 7.0 | 7.0 | 7.0 |
| $Cl^-$ | 113.2 mM | 110.9 mM | 107.7 mM |
| $Na^+$ | 137.5 mM | 134.7 mM | 130.8 mM |
| $Ca^+$ | 1.73 mM | 1.70 mM | 1.65 mM |
| $Mg^+$ | 0.5 mM | 0.49 mM | 0.47 mM |
| $HCO_3^-$ | 38.8 mM | 38.0 mM | 36.9 mM |
| Glucose | 15.3 g/l | 25.0 g/l | 38.8 g/l |
| Lactate | 2.97 mM | 2.91 mM | 2.82 mM |

Examples 37-40

Four-Compartment Bags

Compartment 1:

| | Example 37 | Example 38 | Example 39 | Example 40 |
|---|---|---|---|---|
| $NaHCO_3$ | 95.5 mM | 112 mM | 139 mM | 133 mM |
| $Na_2CO_3$ | 304.5 mM | 258 mM | 661 mM | 607 mM |
| pH | 10.3 | 10.3 | 10.3 | 10.3 |
| Volume | 0.196 l | 0.196 l | 0.098 l | 0.098 l |

Compartment 2:

| | Example 37 | Example 38 | Example 39 | Example 40 |
|---|---|---|---|---|
| HCl | 35.49 mM | 35.49 mM | 36.11 mM | 36.11 mM |
| NaCl | 78.88 mM | 78.88 mM | 71.94 mM | 71.94 mM |
| $CaCl_2 \cdot 2H_2O$ | 1.99 mM | 1.99 mM | 1.88 mM | 1.88 mM |
| $MgCl_2 \cdot 6H_2O$ | 0.57 mM | 0.57 mM | 0.54 mM | 0.54 mM |
| Lactate | — | 3.41 mM | — | 3.22 mM |
| pH | 1.3 | 1.3 | 1.3 | 1.3 |
| Volume | 1.764 l | 1.764 l | 1.862 l | 1.862 l |

Third compartment:

| | Example 37 | Example 38 | Example 39 | Example 40 |
|---|---|---|---|---|
| Glucose | 500 g/l | 500 g/l | 500 g/l | 500 g/l |
| pH | 2-2.5 | 2-2.5 | 2-2.5 | 2-2.5 |
| Volume | 0.062 l | 0.062 l | 0.062 l | 0.062 l |

Fourth compartment:

| | Example 37 | Example 38 | Example 39 | Example 40 |
|---|---|---|---|---|
| Glucose | 500 g/l | 500 g/l | 500 g/l | 500 g/l |
| pH | 2-2.5 | 2-2.5 | 2-2.5 | 2-2.5 |
| Volume | 0.103 l | 0.103 l | 0.103 l | 0.103 l |

Solution, mixed and ready for use:

| | Compartment 1 + 2 + 3 | Compartment 1 + 2 + 4 | Compartment 1 + 2 + 3 + 4 |
|---|---|---|---|
| Example 37 | | | |
| Volume | 2.022 l | 2.063 l | 2.125 l |
| pH | 7.5 | 7.5 | 7.5 |

-continued

| Solution, mixed and ready for use: | | | |
|---|---|---|---|
| | Compartment 1 + 2 + 3 | Compartment 1 + 2 + 4 | Compartment 1 + 2 + 3 + 4 |
| $Cl^-$ | 104.9 mM | 102.8 mM | 99.8 mM |
| $Na^+$ | 137.1 mM | 134.4 mM | 130.5 mM |
| $Ca^+$ | 1.74 mM | 1.70 mM | 1.65 mM |
| $Mg^+$ | 0.50 mM | 0.49 mM | 0.47 mM |
| $HCO_3^-$ | 38.8 mM | 38.0 mM | 36.9 mM |
| Glucose | 15.3 g/l | 25.0 g/l | 38.8 g/l |
| Example 38 | | | |
| Volume | 2.022 l | 2.063 l | 2.125 l |
| pH | 7.5 | 7.5 | 7.5 |
| $Cl^-$ | 104.9 mM | 102.8 mM | 99.8 mM |
| $Na^+$ | 135.6 mM | 132.9 mM | 129.1 mM |
| $Ca^+$ | 1.74 mM | 1.70 mM | 1.65 mM |
| $Mg^+$ | 0.50 mM | 0.49 mM | 0.47 mM |
| $HCO_3^-$ | 35.9 mM | 35.2 mM | 34.1 mM |
| Glucose | 15.3 g/l | 25.0 g/l | 38.8 g/l |
| Lactate | 2.98 mM | 2.92 mM | 2.83 mM |
| Example 39 | | | |
| Volume | 2.022 l | 2.063 l | 2.125 l |
| pH | 7.5 | 7.5 | 7.5 |
| $Cl^-$ | 110.1 mM | 107.9 mM | 104.8 mM |
| $Na^+$ | 137.1 mM | 134.3 mM | 130.5 mM |
| $Ca^+$ | 1.73 mM | 1.70 mM | 1.65 mM |
| $Mg^+$ | 0.50 mM | 0.49 mM | 0.47 mM |
| $HCO_3^-$ | 38.8 mM | 38.0 mM | 36.9 mM |
| Glucose | 15.3 g/l | 25.0 g/l | 38.8 g/l |
| Example 40 | | | |
| Volume | 2.022 l | 2.063 l | 2.125 l |
| pH | 7.5 | 7.5 | 7.5 |
| $Cl^-$ | 110.1 mM | 107.9 mM | 104.8 mM |
| $Na^+$ | 137.5 mM | 134.7 mM | 130.8 mM |
| $Ca^+$ | 1.73 mM | 1.70 mM | 1.65 mM |
| $Mg^+$ | 0.5 mM | 0.49 mM | 0.47 mM |
| $HCO_3^-$ | 38.8 mM | 38.0 mM | 36.9 mM |
| Glucose | 15.3 g/l | 25.0 g/l | 38.8 g/l |
| Lactate | 2.97 mM | 2.91 mM | 2.82 mM |

In summary, based on the above results, the inventors concluded that a stable and biocompatible bicarbonate-based solution can be prepared, provided that it comprises bicarbonate and carbonate in such proportions that the partial pressure of carbon dioxide, $CO_2$, is of the same order of magnitude as the partial pressure of $CO_2$ of the atmosphere.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:

1. A medical solution comprising:
   a first single solution comprising bicarbonate and carbonate in a mass ratio of 1:2.91 to approximately 1:6 such that a partial pressure of carbon dioxide in the first single solution is of the same order of magnitude as a partial pressure of carbon dioxide in the atmosphere, and has a pH of 10.1-10.5; and
   a second single solution comprising an acid,
   wherein said first and second single solutions are mixed after terminal sterilization to form a final solution, wherein said second single solution has a pH of 1.0-1.5 and said final solution has a pH of 7.0-7.6.

2. A medical solution according to claim 1, where said first single solution has a pH of 10.3.

3. A medical solution according to claim 1 or 2, wherein said second single solution has a pH of 1.3.

4. A medical solution according to claim 3, wherein the second single solution comprises HCl.

5. A medical solution according to claim 1, wherein the medical solution further comprises one or more osmotic agents.

6. A medical solution according to claim 5, wherein said one or more osmotic agents are chosen from glucose, glucose polymers, glycerol, xylitol, fructose, amino acids, peptides, proteins, amino sugars, N-acetyl glucose amine (NAG), and combinations thereof.

7. A medical solution according to claim 5, wherein said one or more osmotic agents are arranged in said second single solution before said second single solution is mixed with said first single solution to form the final solution.

8. A medical solution according to claim 5, further comprising a third single solution, and wherein said one or more osmotic agents are arranged in said third single solution, prior to the formation of the final solution.

9. A medical solution according to claim 8, further comprising a fourth single solution, and wherein said one or more osmotic agents are arranged in said fourth single solution.

10. A medical solution according to claim 9, wherein said one or more osmotic agents in said third and/or fourth single solution comprise glucose and/or glucose polymers giving rise to glucose degradation products during terminal sterilization and/or storage, and wherein said third and/or fourth single solutions comprise an acid and have a pH of at least 1.8 and at most 2.6.

11. A medical solution according to claim 9, further comprising one or more electrolytes, and wherein said one or more electrolytes are arranged in said third single solution and/or said fourth single solution, prior to the formation of the final solution.

12. A medical solution according to claim 1 or 5, wherein the medical solution further comprises one or more electrolytes.

13. A medical solution according to claim 12, wherein said one or more electrolytes comprise one or more of the ions of sodium, calcium, potassium, magnesium, and/or chloride.

14. A medical solution according to claim 12, wherein said one or more electrolytes are arranged in said first single solution, prior to the formation of the final solution.

15. A medical solution according to claim 12, wherein said one or more electrolytes are arranged in said second single solution, prior to the formation of the final solution.

16. A medical solution according to claim 1, wherein the first and second single solutions are provided in first and second compartments in a multi-compartment bag before being mixed to form the final solution.

17. A method for producing a medical solution according to claim 1, said method comprising:
   providing said first and second single solutions in separate compartments; and thereafter
   terminally sterilizing said first and second single solutions.

18. A method according to claim 17, wherein said step of terminally sterilizing comprises heat sterilization and/or radiation sterilization.

19. A method according to claim 17, wherein said step of terminally sterilizing comprises heat sterilization at a temperature of at least 100° C.

20. A method according to claim 17, wherein said first and second single solutions, after terminal sterilization, are mixed to form a final solution.

21. A method according to claim 17, wherein the first and second single solutions are provided in first and second compartments in a multi-compartment bag before being mixed to form the final solution.

22. A multi-compartment bag comprising the medical solution according to one of claim 1, 8, or 9.

23. A medical solution according to claim 1, wherein the mass ratio is approximately 1:6.

24. A method for producing a medical solution according to claim 8, wherein the first, second, and third single solutions are provided in first, second, and third compartments in a multi-compartment bag before being mixed to form the final solution.

25. A method according to claim 24, wherein said first, second, and third single solutions, after terminal sterilization, are mixed to form a final solution.

26. A method according to claim 25, wherein the first, second, and third single solutions are provided in first, second, and third compartments in a multi-compartment bag before being mixed to form the final solution.

27. A method for producing a medical solution according to claim 9, wherein the first, second, third, and fourth single solutions are provided in first, second, third, and fourth compartments in a multi-compartment bag before being mixed to form the final solution.

28. A method according to claim 27, wherein said first, second, and fourth single solutions, after terminal sterilization, are mixed to form a final solution.

29. A method according to claim 27, wherein said first, second, third, and fourth single solutions, after terminal sterilization, are mixed to form a final solution.

30. A method for producing a medical solution according to claim 27, wherein the first, second, and third single solutions, after terminal sterilization, are mixed to form a final solution.

31. A method according to claim 29, wherein the first, second, third, and fourth single solutions are provided in first, second, third, and fourth compartments in a multi-compartment bag before being mixed to form the final solution.

* * * * *